(12) United States Patent
Yokosawa et al.

(10) Patent No.: US 10,696,751 B2
(45) Date of Patent: *Jun. 30, 2020

(54) SOLID PREPARATION CONTAINING ALKYL CELLULOSE AND METHOD FOR PRODUCING THE SAME

(71) Applicant: Shin-Etsu Chemical Co., Ltd., Tokyo (JP)

(72) Inventors: Takuya Yokosawa, Niigata-ken (JP); Naosuke Maruyama, Niigata-ken (JP); Akira Kitamura, Niigata-ken (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 189 days.

This patent is subject to a terminal disclaimer.

(21) Appl. No.: 15/450,151

(22) Filed: Mar. 6, 2017

(65) Prior Publication Data

US 2017/0260295 A1  Sep. 14, 2017

(30) Foreign Application Priority Data

Mar. 9, 2016 (JP) .................................. 2016-045746

(51) Int. Cl.
  *C08B 11/02* (2006.01)
  *C11D 3/22* (2006.01)
  *A61K 47/38* (2006.01)
  *C11D 17/00* (2006.01)
  *A61K 9/20* (2006.01)
  *A61K 31/167* (2006.01)

(52) U.S. Cl.
  CPC ............ *C08B 11/02* (2013.01); *A61K 9/2054* (2013.01); *A61K 9/2095* (2013.01); *A61K 31/167* (2013.01); *A61K 47/38* (2013.01); *C11D 3/225* (2013.01); *C11D 17/0073* (2013.01)

(58) Field of Classification Search
  CPC .............................. C08B 11/02; A61K 31/717
  USPC .................................................... 536/99, 100
  See application file for complete search history.

(56) References Cited

U.S. PATENT DOCUMENTS

| | | | |
|---|---|---|---|
| 5,372,998 A * | 12/1994 | Kokubo | ............... A61K 9/2866 424/468 |
| 5,574,150 A | 11/1996 | Yaginuma et al. | |
| 9,713,593 B2 * | 7/2017 | Yokosawa | ............ A61K 31/167 |
| 10,058,509 B2 * | 8/2018 | Yokosawa | ............ A61K 31/167 |
| 2007/0179292 A1 * | 8/2007 | Spencer | .................. C08B 11/02 536/88 |
| 2012/0232167 A1 | 9/2012 | Takeuchi et al. | |
| 2014/0034760 A1 | 2/2014 | Takeuchi et al. | |
| 2016/0113875 A1 * | 4/2016 | Yokosawa | ............ A61K 31/167 514/630 |

FOREIGN PATENT DOCUMENTS

| | | |
|---|---|---|
| EP | 2907508 | 8/2015 |
| EP | 3011956 | 4/2016 |
| JP | H06-316535 A | 11/1994 |
| JP | 2002-541270 A | 3/2002 |
| JP | 2010-254756 A | 11/2010 |
| WO | 00/59947 A | 10/2000 |
| WO | WO 2011/065350 A1 | 6/2011 |

OTHER PUBLICATIONS

Extended European Search Report for corresponding European Application No. 17158254.7 dated May 30, 2017, 9 pages.
Japanese Office Action, Application No. 2017-045045, dated Nov. 6, 2019.
Takuya Yokosawa and Naosuke Maruyuma, "Application of Novel Methyl Cellulose to Dry Binder", Proceedings of the Thirty-Second Symposium, for Medicaments and Particle Design, 2015, vol. 32, pp. 18-19m published by Medicaments and Particle Design Office in The Society of Powder Technology, Japan, on Oct. 9, 2015.

* cited by examiner

*Primary Examiner* — Patrick T Lewis
(74) *Attorney, Agent, or Firm* — Rimon, P.C.

(57) ABSTRACT

Provided are a solid preparation comprising an alkyl cellulose which provides excellent moldability and disintegrability even in a small amount of the alkyl cellulose, and a production method therefor. Specifically, provided are a solid preparation having an alkyl cellulose having a specific surface area by BET method of 0.5 to 10.0 m²/g and a dissolution start temperature of 5 to 27° C.; and a method for producing a solid preparation having the steps of: mixing a cellulose pulp and a first alkali metal hydroxide solution with stirring to obtain alkali cellulose, reacting the alkali cellulose with an alkylating agent to obtain a first reaction mixture, mixing the first reaction mixture and a second alkali metal hydroxide solution with stirring and without further addition of any alkylating agent to obtain a second reaction mixture, and pulverizing an alkyl cellulose isolated from the second reaction mixture to obtain an alkyl cellulose.

9 Claims, 1 Drawing Sheet

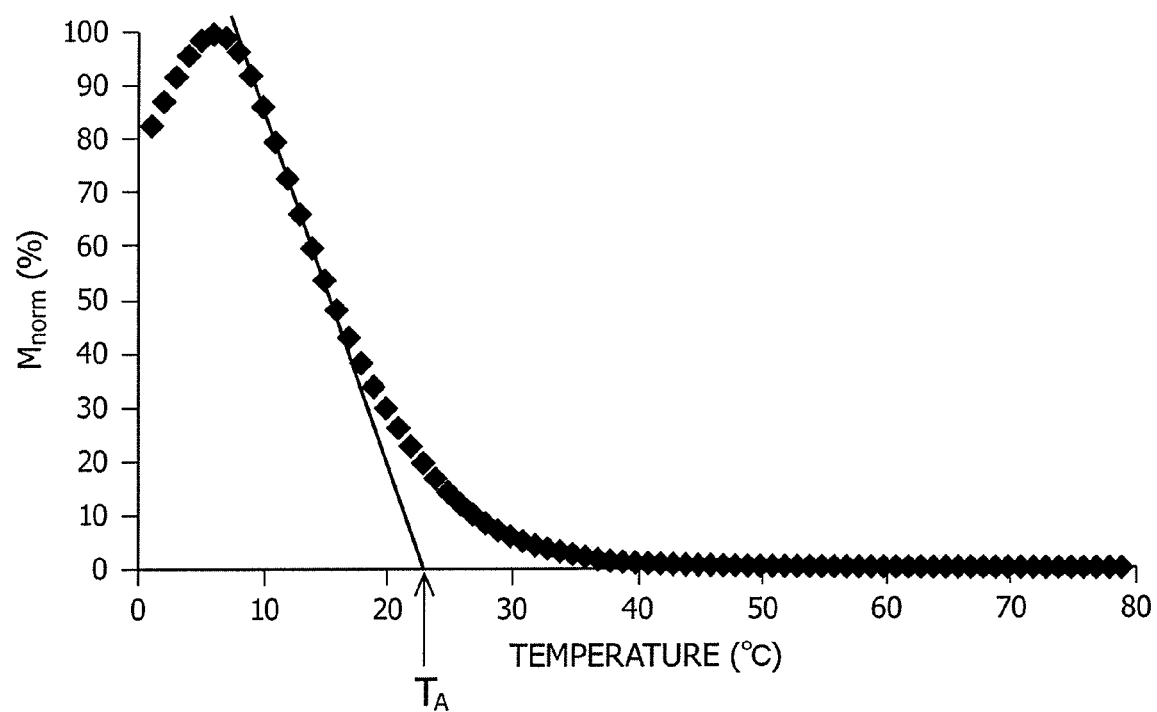

SOLID PREPARATION CONTAINING ALKYL CELLULOSE AND METHOD FOR PRODUCING THE SAME

FIELD

The present invention relates to a solid preparation containing an alkyl cellulose in the fields of pharmaceutical products, foods and health foods, wherein the alkyl cellulose provides high moldability and good disintegrability even in a small amount of the alkyl cellulose; and a method for producing the solid preparation.

BACKGROUND

In the fields of pharmaceutical products, foods and health foods, the method for producing a solid preparation, especially a tablet, includes dry direct tableting in which a mixture of a drug and an additive is directly subjected to tableting; dry granulation tableting in which a mixture of a drug and an additive is subjected to roll compression (dry granulation), then disintegration and tableting; and wet granulation tableting in which a mixture of a drug and an additive is granulated together with a binder solution or an appropriate solvent such as water, and the resulting granules are dried and then subjected to tableting. The wet granulation tableting involves an agitation granulator or a fluidized bed granulator.

The dry direct tableting and the dry granulation tableting have been increasingly adopted in many cases because the methods are applicable to a drug susceptible to water and include a simple process for easy process control. However, the methods typically require a larger amount of an additive than the wet granulation tableting in order to ensure moldability. Examples of the additive having high moldability include crystalline cellulose (JP 06-316535A), hydroxyalkyl cellulose fine particles (WO 2011/065350A1) and low-substituted hydroxypropyl cellulose (JP 2010-254756A).

In recent years, tablets are downsized for easy administration, so that the content of a binder or the like is likely to be suppressed. To address such a trend, there is a demand for a binder that increases the hardness of a tablet at a small content. In addition, a tablet administered is desired to be immediately disintegrated in terms of bioavailability.

SUMMARY

The crystalline cellulose disclosed in JP 06-316535A is required to be added in a large amount to ensure moldability, and cannot be applied to a solid preparation containing a large amount of drug and a small tablet. The hydroxyalkyl cellulose fine particles disclosed in WO 2011/065350A1 have excellent moldability but poor disintegrability. The low-substituted hydroxypropyl cellulose disclosed in JP 2010-254756A has excellent disintegrability but insufficient moldability. As described above, it is conventionally difficult to satisfy both high moldability and excellent disintegrability with addition of a small amount.

In view of the above circumstances, the present invention provides a solid preparation containing an alkyl cellulose which provides excellent moldability and excellent disintegrability at a small content of the alkyl cellulose, and a method for producing the solid preparation.

As a result of intensive studies for solving the above problems, the present inventors have found that the above object is achieved by using an alkyl cellulose having a particular specific surface area and a particular dissolution start temperature, and have completed the present invention.

In an aspect of the present invention, there is provided a solid preparation comprising an alkyl cellulose having a specific surface area determined by BET method of 0.5 to 10.0 $m^2/g$ and a dissolution start temperature of 5 to 27° C.

In another aspect of the present invention, there is provided a method for producing a solid preparation, comprising the steps of: mixing a cellulose pulp and a first alkali metal hydroxide solution with stirring to obtain alkali cellulose; reacting the alkali cellulose with an alkylating agent to obtain a first reaction mixture; mixing the first reaction mixture and a second alkali metal hydroxide solution with stirring and without further addition of any alkylating agent to obtain a second reaction mixture; isolating an alkyl cellulose from the second reaction mixture; pulverizing the alkyl cellulose to obtain a pulverized alkyl cellulose; depolymerizing the pulverized alkyl cellulose to obtain a low-polymerization-degree alkyl cellulose; pulverizing the low-polymerization-degree alkyl cellulose to obtain a pulverized low-polymerization-degree alkyl cellulose; and subjecting a mixture or granule containing the pulverized low-polymerization-degree alkyl cellulose and a drug to dry direct tableting or dry granulation tableting; wherein a ratio of a weight of a first alkali metal hydroxide in the first alkali metal hydroxide solution to a total weight of the first alkali metal hydroxide in the first alkali metal hydroxide solution and a second alkali metal hydroxide in the second alkali metal hydroxide solution is 50 to 86%.

In the present invention, with respect to the solid preparation comprising an alkyl cellulose, the alkyl cellulose provides high moldability and excellent disintegrability, so that a tablet produced by dry direct tableting or dry granulation tableting can have increase in tablet hardness and reduction in tablet disintegration time. The solid preparation is particularly effective for a formulation containing a limited amount of an additive, such as a formulation required to contain a high content of drug, a formulation of a small tablet, and a formulation of a granule-containing tablet required to be prepared by tableting at a low tableting pressure. In the solid preparation comprising the alkyl cellulose, the alkyl cellulose provides high moldability at the time of dry granulation before tableting, so that flakes are obtained at high yield in the step of dry granulation. In addition, when the obtained flakes are disintegrated to produce granules or fine granules, generation of fine powder is reduced, and tablets produced by tableting of the dry granulated powder have high tablet hardness.

BRIEF DESCRIPTION OF THE DRAWINGS

FIGURE exhibits a graph showing a method of determining the dissolution start temperature of methyl cellulose.

DETAILED DESCRIPTION

The present invention will now be described in further detail.

An alkyl cellulose has a specific surface area determined by BET method (multipoint BET method) of 0.5 to 10.0 $m^2/g$, preferably 0.8 to 10.0 $m^2/g$, more preferably 1.4 to 8.0 $m^2/g$, even more preferably 1.8 to 7.0 $m^2/g$. When the specific surface area is less than 0.5 $m^2/g$, an intended moldability is not obtained. When the specific surface area is more than 10.0 $m^2/g$, the mixing properties with a drug and flowability deteriorate during production of a tablet.

The specific surface area can be evaluated by BET method (multipoint BET method) in which low-temperature and low-moisture physical adsorption of an inert gas is utilized and molecules whose adsorption occupation area is known are allowed to adsorb to the surface of sample powder particles at the temperature of liquid nitrogen to determine the specific surface area of the sample from the amount of the adsorbed molecules. For example, the specific surface area can be determined in accordance with "Method 2: The volumetric method" in "Specific Surface Area by Gas Adsorption" of General Tests described in the Japanese Pharmacopoeia Sixteenth Edition, by using an automatic specific surface area/pore distribution analyzer, TriStar II 3020 manufactured by Micromeritics.

The alkyl cellulose has a dissolution start temperature of 5 to 27° C., preferably 15 to 27° C., more preferably 18 to 27° C., even more preferably 18 to 24° C. When the dissolution start temperature is less than 5° C., it is difficult to prepare a 2% by weight aqueous solution of alkyl cellulose for viscosity measurement at 20° C. When the dissolution start temperature is more than 27° C., an alkyl-cellulose-containing tablet has a prolonged disintegration time. An alkyl cellulose has such a dissolution property in a solvent that the alkyl cellulose is not dissolved in the solvent of high temperature but starts to be dissolved as the temperature of the solvent decreases. Meanwhile, it is generally known that when a tablet containing a water-soluble polymer powder is disintegrated in the oral cavity by, for example, saliva or water, the water-soluble polymer is dissolved to exhibit viscosity, which prevents water from permeating into the tablet to prolong the disintegration time. Commercially available methyl cellulose typically have a dissolution start temperature of more than 27° C., while in the present invention, the alkyl cellulose such as methyl cellulose has a low dissolution start temperature and hardly exhibits viscosity by dissolution at a temperature of more than 27° C. For this reason, it is considered that when a tablet is taken, the alkyl cellulose having a dissolution start temperature of less than the body temperature is not dissolved, so that the viscosity is not exhibited and the disintegration time is not prolonged.

A dissolution temperature as a physical property associated with the dissolution start temperature is the temperature at which an alkyl cellulose is completely dissolved. Thus, the alkyl cellulose exhibits viscosity before reaching the dissolution temperature. For this reason, the dissolution start temperature defined as the start of viscosity expression of an alkyl cellulose is considered to be more closely related to the disintegrability of a tablet, so that the dissolution start temperature is specified in the present invention. Substances similar to the alkyl cellulose include hydroxyalkyl alkyl celluloses such as hydroxypropyl methyl cellulose, but the hydroxypropyl methyl cellulose has a dissolution start temperature of about 40° C. or more, which is higher than that of the alkyl cellulose in the present invention, and thus has poor disintegrability.

The dissolution start temperature can be determined by plotting torque generated when an alkyl cellulose dispersed in hot water is cooled, against temperature. The dissolution start temperature can be determined by using a rheometer such as MCR301 manufactured by Anton Paar.

The dissolution start temperature of an alkyl cellulose is specifically determined by the method comprising the steps of: adjusting the temperature of a CC27 measurement cup (CC27/T200/AL, a cylindrical aluminum container having a diameter of 29 mm and a height of 68 mm) placed in the sample-measuring section of a rheometer to 80° C.; accurately weighing 4.8 g of an alkyl cellulose on pharmaceutical paper (when viscosity at 20° C. of 2% by weight solution of the alkyl cellulose is less than 7.3 mPa·s); adding the weighed alkyl cellulose and 35.2 g of hot water (98° C.) into the measurement cup taken out of the rheometer to make a total weight of 40.0 g (when viscosity at 20° C. of 2% by weight solution of the alkyl cellulose is less than 7.3 mPa·s); thoroughly mixing the resulting mixture with stirring by using a blade type measurement jig (ST24-2D/2V/2V-30) to allow the alkyl cellulose to be completely dispersed in the hot water to obtain a dispersion; placing the measurement cup and the blade type measurement jig in the sample-measuring section of the rheometer; stirring the dispersion at 400 rpm for 5 minutes while controlled at 80° C.; and then stirring the dispersion at 400 rpm while cooling the sample-measuring section to 1° C. at the decrease rate of 1° C./min with a Peltier temperature controller. The torque vales are recorded at a point per minute in the range of from 80° C. to 1° C., and the increase of torque vales is shown as a function of temperature. The obtained data are normalized in accordance with the following equation.

$$M_{norm}(\%) = \{(M-M_i)/(M_{max}-M_i)\} \times 100$$

In the equation, $M_{norm}$ represents a normalized torque value; M represents a torque value measured at each temperature; $M_i$ represents a torque value at the initial temperature (80° C.); and $M_{max}$ represents the maximum torque value of the obtained torque values. A graph is prepared where the horizontal axis represents temperature and the vertical axis represents Worm, and a linear regression is prepared from five or more data in a temperature range of 5° C. The intersection of a linear regression having a maximum slope and a sufficient coefficient of correlation ($R^2$=0.99 or more) and the X axis (temperature axis) is defined as the dissolution start temperature. FIGURE shows the method of determining the dissolution start temperature of an alkyl cellulose. In this example, the dissolution start temperature is $T_A$.

The optimum concentration for measuring the dissolution start temperature varies depending on the viscosity at 20° C. of 2% by weight solution of an alkyl cellulose to be measured. This is because when the dissolution start temperature of an alkyl cellulose having a low viscosity is measured with a low concentration dispersion, torque values measured are too low to obtain proper measurement results. In order to obtain proper test results, the measurement is preferably carried out at such a concentration as to provide a maximum torque value ($M_{max}$) of 1,000 μNm or more. Specifically, the measurement is carried out for a 12% by weight alkyl cellulose dispersion (i.e. a 12% by weight alkyl cellulose solution as a result of complete dissolution of the alkyl cellulose) when a viscosity at 20° C. of 2% by weight solution of the alkyl cellulose is less than 7.3 mPa·s; a 6% by weight alkyl cellulose dispersion when a viscosity at 20° C. of 2% by weight solution of the alkyl cellulose is 7.3 to 79 mPa·s; a 3% by weight alkyl cellulose dispersion when a viscosity at 20° C. of 2% by weight solution of the alkyl cellulose is 80 to 550 mPa·s; a 2% by weight alkyl cellulose dispersion when a viscosity at 20° C. of 2% by weight solution of the alkyl cellulose is 551 to 100,000 mPa·s; and an 1% by weight alkyl cellulose dispersion when a viscosity at 20° C. of 2% by weight solution of the alkyl cellulose is more than 100,000 mPa·s.

The viscosity at 20° C. of a 2% by weight aqueous solution of the alkyl cellulose is not particularly limited. It is preferably 1 to 150,000 mPa·s, more preferably 1 to 80,000 mPa·s, even more preferably 1 to 15 mPa·s, particularly preferably 2 to 8 mPa·s from the standpoint of moldability for producing tablets and disintegrability. A product having a high viscosity (1,000 to 150,000 mPa·s) has excellent disintegrability, while a product having a low viscosity (1 to 15 mPa·s) has excellent moldability and grindability (i.e. ability to grind particles easily). When the viscosity at 20° C. of a 2% by weight aqueous solution is 600 mPa·s or more, the viscosity can be determined in accordance with "Viscosity measurement by rotational viscometer" in "Viscosity Determination" of General Tests described in the Japanese Pharmacopoeia Sixteenth Edition, by using a single cylinder-type rotational viscometer. When the viscosity at 20° C. of a 2% by weight aqueous solution is less than 600 mPa·s, the viscosity can be determined in accordance with "Viscosity measurement by capillary tube viscometer" in "Viscosity Determination" of General Tests described in the Japanese Pharmacopoeia Sixteenth Edition, by using an Ubbelohde-type viscometer.

A volume average particle size of the alkyl cellulose, determined by dry laser diffractometry, is not particularly limited. It is preferably 1 to 50 μm, more preferably 1 to 35 μm, even more preferably 1 to 25 μm. When the volume average particle size is less than 1 μm, mixability with a drug and flowability may be deteriorated for the production of tablets. When the average volume particle size is more than 50 μm, a sufficient specific surface area may not be ensured and intended moldability may not be provided. The volume average particle size is an average particle size in terms of volume, and is calculated in accordance with the equation $\{\Sigma(nD^3)/\Sigma n\}^{1/3}$ as described, for example, in "Kaitei Zoho, Funtai Bussei Zusetsu (Physical Properties of Powder with Illustrations, revised and enlarged edition)" edited by the Society of Powder Technology, Japan and the Association of Powder Process Industry and Engineering, Japan, published by Nikkei Gijutsu Tosho, 1985, page 88. In the equation, D represents the diameter of a particle, n is the number of particles having the diameter D, and $\Sigma n$ is the total number of particles. $D_{50}$ is a particle size (average particle size) at an integrated value of 50% in a particle size distribution. The average particle size can be determined by dry laser diffractometry. The average particle size can be determined by a method comprising the step of applying laser beams to a powder sample sprayed by compressed air to measure diffraction intensities, wherein the volume average particle size is calculated on basis of the diffraction intensities. The method involves, for example, MASTERSIZER 3000 manufactured by Malvern in England or HELOS manufactured by Sympatec in Germany.

A loose buke density of the alkyl cellulose is not particularly limited. The loose bulk density is preferably 0.01 to 0.30 g/mL, more preferably 0.03 to 0.25 g/mL, even more preferably 0.03 to 0.20 g/mL, from the standpoint of high moldability. The loose bulk density is a bulk density in a loosely packed state and is determined by the method comprising the steps of: evenly feeding a sample sieved through a JIS 22-mesh sieve having a mesh size of 710 μm into a cylindrical container being made of stainless steel and having a diameter of 5.03 cm and a height of 5.03 cm (a capacity of 100 ml) 23 cm above from the top surface of the container; and then leveling off the top surface of the container for weighing.

The degree of substitution (DS) for the alkyl cellulose is not particularly limited. The degree of substitution (DS) is preferably 1.61 to 2.03, more preferably 1.74 to 2.03 from the standpoint of the desirable dissolution start temperature. When the DS is less than 1.61, an alkyl cellulose may have a lower solubility in water. When the DS is more than 2.03, larger amounts of an alkylating agent and an alkali metal hydroxide are required so that there may be economically disadvantageous.

Generally, the DS is a degree of substitution and represents an average number of hydroxy groups substituted by methoxy groups or ethoxy groups per anhydroglucose ring unit of a cellulose. As for the degree of substitution of alkyl group of an alkyl cellulose, for example, when the alkyl cellulose is methyl cellulose, the degree of substitution of methoxy group can be calculated from the value determined by the determination method under the heading of "methyl cellulose" in accordance with the Japanese Pharmacopoeia Sixteenth Edition.

The alkyl cellulose is a nonionic polymer obtained by etherification of some hydroxy groups on a glucose ring of a cellulose, and exemplified by methyl cellulose and ethyl cellulose. Of them, methyl cellulose is particularly preferred from the standpoint of moldability and disintegrability.

Next, the method for producing an alkyl cellulose will be described.

Typically, an alkyl cellulose can be produced by bringing a starting material cellulose pulp into contact with an alkali metal hydroxide solution to obtain alkali cellulose and then reacting the alkali cellulose with an etherifying agent. In the present invention, an alkali metal hydroxide solution is blended in two or more steps and an alkylating agent is added in one step, to obtain an alkyl cellulose having a low dissolution start temperature.

Specifically, an intended alkyl cellulose can be produced by the method comprising the steps of: mixing a cellulose pulp and a first alkali metal hydroxide solution with stirring to obtain alkali cellulose; reacting the alkali cellulose with an alkylating agent to obtain a first reaction mixture; mixing the first reaction mixture and a second alkali metal hydroxide solution with stirring and without further addition of any alkylating agent to obtain a second reaction mixture; and isolating an alkyl cellulose from the second reaction mixture; wherein a ratio of a weight of a first alkali metal hydroxide in the first alkali metal hydroxide solution to a total weight of the first alkali metal hydroxide in the first alkali metal hydroxide solution and a second alkali metal hydroxide in the second alkali metal hydroxide solution is 50 to 86%.

The cellulose pulp is exemplified by wood pulp and linter pulp, and is used as a starting material for the production of a typical cellulose ether. The intrinsic viscosity as an index of the polymerization degree of a cellulose pulp can be appropriately selected depending on the viscosity of an aqueous solution of an intended cellulose ether, and is preferably 1,000 to 2,200 ml/g, more preferably 1,300 to 2,000 ml/g at 25° C. The intrinsic viscosity of a cellulose pulp can be determined by a method in accordance with method A in JIS P8215.

The cellulose pulp contains cellulose and water. In the present specification, the amount of "the cellulose in a cellulose pulp" can be calculated from the dry matter content determined in accordance with Pulps—Determination of dry matter content in JIS P8203: 1998. The dry matter content is determined by the method comprising the step of drying a sample at 105±2° C. until the weight of the sample reaches a constant value to find out the ratio (%) of the weight after drying to the weight before drying as the dry matter content (%).

The cellulose pulp is preferably a cellulose pulp powder prepared by pulverization with a pulverizer. The pulp pulverizer may be any pulverizer that can make a cellulose pulp into a powder. Examples of the pulverizer may include a knife mill, a cutting mill, a hammer mill, a ball mill and a vertical roller mill. The cellulose pulp powder preferably has a weight average particle size $D_{50}$ of preferably 30 to 400 µm. The weight average particle size $D_{50}$ of a cellulose pulp powder is determined by the method comprising the steps of: installing a plurality of test sieves having various mesh sizes in a Ro-Tap sieve shaker in accordance with JIS Z8801; placing the cellulose pulp powder on the uppermost sieve; and vibrating or tapped the cellulose pulp powder for sieving to obtain the weight on each sieve and the weight under the sieves for the weight distribution. The average particle size at an integrated value of 50% is determined as the weight average particle size $D_{50}$.

Next, the step of mixing a cellulose pulp and a first alkali metal hydroxide solution with stirring to obtain alkali cellulose will be described.

The alkali metal hydroxide solution is divided into, for example, a first alkali metal hydroxide solution and a second alkali metal hydroxide solution, and blended in two steps. The alkali metal hydroxide solution is not particularly limited and is exemplified by a sodium hydroxide solution and a potassium hydroxide solution. An aqueous sodium hydroxide solution is preferred from the standpoint of economy. The kind of the first alkali metal hydroxide in the first alkali metal hydroxide solution is preferably the same as the kind of the second alkali metal hydroxide in the second alkali metal hydroxide solution, and for example, each of the first and second alkali metal hydroxides is sodium hydroxide. On the other hand, the first and second alkali metal hydroxides may be a combination of different kinds, and for example, sodium hydroxide and potassium hydroxide are used as the first and second alkali metal hydroxides, respectively.

The blending of the alkali metal hydroxide solution is preferably adding of the alkali metal hydroxide solution to a cellulose pulp, and is exemplified by direct dropping of the alkali metal hydroxide solution and spraying of the alkali metal hydroxide solution. The spraying is preferred from the standpoint of good uniformity of the resulting alkali cellulose.

The concentration of the alkali metal hydroxide in the alkali metal hydroxide solution is preferably 10 to 60% by weight, more preferably 30 to 50% by weight from the standpoint of etherification efficiency and handleability. The first alkali metal hydroxide and the second alkali metal hydroxide preferably have the same concentrations, but may have different concentrations.

The step of mixing a cellulose pulp and an alkali metal hydroxide solution with stirring is preferably carried out in a reactor having an inner stirring structure. The reactor is preferably equipped with a measurement device such as a device capable of measuring the inner temperature.

Before mixing the first alkali metal hydroxide solution and the cellulose pulp with stirring, it is preferred that oxygen in the reactor be removed by a vacuum pump or the like and be replaced with an inert gas, preferably nitrogen, to suppress depolymerization which can proceed in the presence of an alkali metal hydroxide and oxygen.

Regarding the amount of the first alkali metal hydroxide solution, a molar ratio of the first alkali metal hydroxide to the cellulose in the cellulose pulp (first alkali metal hydroxide/cellulose) is preferably 2.0 to 4.0, more preferably 2.7 to 3.5. When the molar ratio of the first alkali metal hydroxide to the cellulose is more than 4.0, an alkyl cellulose having a low dissolution start temperature may not be produced.

The ratio of the weight of the first alkali metal hydroxide in the first alkali metal hydroxide solution to the total weight of the first alkali metal hydroxide in the first alkali metal hydroxide solution and the second alkali metal hydroxide in the second alkali metal hydroxide solution is 50 to 86%, preferably 65 to 80%, more preferably 65 to 75%. When the ratio of the weight of the first alkali metal hydroxide to the total weight of the first and second alkali metal hydroxides is less than 50%, the dissolution start temperature becomes excessively low. When the ratio is more than 86%, an alkyl cellulose having a low dissolution start temperature cannot be produced.

The inside temperature of the reactor during blending of the cellulose pulp with the first alkali metal hydroxide, preferably during addition of the first alkali metal hydroxide solution to the cellulose pulp, is preferably 10 to 80° C., more preferably 30 to 70° C. from the standpoint of a uniform alkali cellulose.

The blending rate of the first alkali metal hydroxide in the first alkali metal hydroxide solution means the molar amount of the first alkali metal hydroxide added per unit time relative to 1 mol of the cellulose in the cellulose pulp, and is preferably 1.5 to 48 [mol/mol·hr], more preferably 4.8 to 18.6 [mol/mol·hr], even more preferably 8 to 15 [mol/mol·hr] from standpoint of uniform mixing of the first alkali metal hydroxide solution in the system. After the addition of the first alkali metal hydroxide solution is over, the mixing with stirring may be continued for another 5 to 30 minutes to obtain the alkali cellulose in more uniform state.

To suppress local generation of heat in the reactor, an organic solvent not affecting the alkylation, such as dimethyl ether, may be added to the system before, during, or after the addition of the first alkali metal hydroxide solution.

Next, the produced alkali cellulose is reacted with an alkylating agent to obtain a first reaction mixture.

Examples of the alkylating agent include a methylating agent such as methyl chloride, dimethyl sulfate and methyl iodide; and an ethylating agent such as ethyl chloride, diethyl sulfate and ethyl iodide. Methyl chloride is preferred from the standpoint of obtaining an alkyl cellulose having a low dissolution start temperature and economy.

The inside temperature of the reactor during the reaction with the alkylating agent is preferably 40 to 90° C., more preferably 50 to 80° C. from the standpoint of reaction control.

Regarding the molar amount of the alkylating agent, the molar ratio of the alkylating agent to the total molar amount of the first and second alkali metal hydroxides (alkylating agent/total alkali metal hydroxide) is preferably 0.8 to 1.5, more preferably 1.0 to 1.3. When the molar ratio (alkylating agent/total alkali metal hydroxide) is less than 0.8, an intended number of alkyl groups may not be added by substitution. When the molar ratio is more than 1.5, the excess amount of the alkylating agent may be economically disadvantageous.

Regarding the blending of the alkylating agent, addition of the alkylating agent to the alkali cellulose is preferred. The period of time for adding the alkylating agent is preferably 30 to 120 minutes, more preferably 40 to 90 minutes from the standpoint of reaction control and productivity.

The alkyl cellulose in the first reaction mixture has a degree of substitution (DS) of alkyl group of preferably 0.75 to 1.68, more preferably 0.81 to 1.68, even more preferably 0.99 to 1.37 to obtain an intended dissolution start temperature.

Subsequently, the first reaction mixture is blended with a second alkali metal hydroxide solution with stirring in the absence of further blending of any alkylating agent to obtain a second reaction mixture. The first reaction mixture to be blended with the second alkali metal hydroxide solution may be the reaction mixture in which some or all of the alkylating agent has been added.

The timing of blending the first reaction mixture with the second alkali metal hydroxide solution, which is the timing of starting to blend the second alkali metal hydroxide solution, is preferably after 80% by weight or more of the total amount of the alkylating agent to be blended has been added, more preferably after the completion of the addition of the alkylating agent. When the timing of starting to add the second alkali metal hydroxide solution is before 80% by weight of the total amount of the alkylating agent to be blended has been added, an alkyl cellulose having a low dissolution start temperature may not be produced.

Regarding the amount of the second alkali metal hydroxide in the second alkali metal hydroxide solution, a molar ratio of the second alkali metal hydroxide to the cellulose in the cellulose pulp (second alkali metal hydroxide/cellulose) is preferably 0.65 to 2.0, more preferably 0.88 to 1.48. When the molar ratio of the second alkali metal hydroxide to the cellulose is less than 0.65, an alkyl cellulose having a low dissolution start temperature may not be produced.

The inside temperature of the reactor at the start of the blending of the second alkali metal hydroxide solution with the first reaction mixture, preferably at the start of the addition of the second alkali metal hydroxide solution to the first reaction mixture, is preferably 65 to 90° C., more preferably 75 to 85° C. from the standpoint of the production of an alkyl cellulose having a low dissolution start temperature. When the inside temperature of the reactor at the start of the addition of the second alkali metal hydroxide solution is less than 65° C., an alkyl cellulose having a low dissolution start temperature may not be produced. When the inside temperature of the reactor at the start of the addition is more than 90° C., heat generation due to mercerization by the alkali metal hydroxide or exothermic reaction by alkylation may not be controlled. The inside temperature of the reactor at the completion of the blending of the second alkali metal hydroxide solution is preferably 80° C. to 100° C., more preferably 85 to 95° C. from the standpoint of the production of an alkyl cellulose having a low dissolution start temperature. The temperature at the start of the addition is lower than the temperature at the completion of the addition, and the temperature difference therebetween is preferably 3 to 20° C., more preferably 4 to 15° C.

The blending rate of the second alkali metal hydroxide in the second alkali metal hydroxide solution means the molar amount of the second alkali metal hydroxide blended with the first reaction mixture per unit time relative to 1 mol of the cellulose in the cellulose pulp, and is preferably 0.5 to 9.6 [mol/mol·hr], more preferably 1.0 to 6.5 [mol/mol·hr], even more preferably 1.0 to 3.5 [mol/mol·hr]. When the blending rate of the second alkali metal hydroxide is less than 0.5 [mol/mol·hr], the period of time for blending the second alkali metal hydroxide becomes long so that the reaction time may be extended. When the blending rate of the second alkali metal hydroxide is more than 9.6 [mol/mol·hr], an alkyl cellulose having a low dissolution start temperature may not be produced.

In the step of blending the second alkali metal hydroxide solution with the first reaction mixture, it is preferred that the inside temperature of the reactor be increased at a constant rate from the start to the completion of the blending of the second alkali metal hydroxide solution from a standpoint of the production of an alkyl cellulose having a low dissolution start temperature. The temperature increase rate is preferably 3.0 to 50° C./hr, more preferably 8.0 to 45° C./hr, even more preferably 8.0 to 30° C./hr.

Typically, the alkali cellulose prepared by mixing a cellulose pulp with an alkali metal hydroxide solution is etherified with an alkylating agent to produce an alkyl cellulose. The alkylating agent in the reaction system is gradually consumed as the etherification proceeds. When the inside temperature of the reactor is constant, the reaction rate of the etherification gradually decreases as the alkylating agent is consumed in the reaction system. On this account, by blending the second alkali metal hydroxide solution while increasing the inside temperature of the reactor at a constant rate, the decrease of the reaction rate of the etherification caused by the consumption of the alkylating agent in the reaction system is suppressed so that the reaction rate of the etherification associated with the blending of the second alkali metal hydroxide solution is relatively increased. Thus, an alkyl cellulose having a low dissolution start temperature can be produced.

After the blending of the second alkali metal hydroxide solution is completed, the mixing with stirring is preferably continued to complete the etherification.

The inside temperature of the reactor during the mixing with stirring after the blending of the second alkali metal hydroxide solution is completed, is preferably 80 to 120° C., more preferably 85 to 100° C. from the standpoint of reaction controllability. To complete the reaction, the mixture is preferably heated after the blending of the second alkali metal hydroxide solution is completed.

The period of time for the mixing with stirring after the blending of the second alkali metal hydroxide solution is completed, is preferably 10 to 60 minutes, more preferably 20 to 40 minutes from the standpoint of productivity.

The obtained second reaction mixture may be purified in the same manner as the usual purification of a crude alkyl cellulose, to obtain an alkyl cellulose. The purification method and the purification device are not particularly limited. In consideration of cost efficiency, the purification can be carried out by using preferably water, more preferably hot water (preferably of 60 to 100° C.). Specifically, the purification can be carried out by the method comprising the steps of: mixing the second reaction mixture with water with stirring in a container to dissolve salts generated as by-products; and subjecting the suspension discharged from the container to a separation operation to remove the salts.

After the purification, the product may be optionally dried. The drying method and the dryer are not particularly limited. The temperature of the alkyl cellulose during drying is preferably 40 to 80° C.

The viscosity at 20° C. of a 2% by weight aqueous solution of the alkyl cellulose obtained after the purification step or the optional drying step is not particularly limited. The viscosity is preferably more than 20 mPa·s, more preferably 50 to 150,000 mPa·s. When the viscosity at 20° C. of the 2% by weight aqueous solution of an alkyl cellulose is 600 mPa·s or more, the viscosity may be determined in accordance with "Viscosity measurement by rotational viscometer" in "Viscosity Determination" of General Tests described in the Japanese Pharmacopoeia Sixteenth Edition, by using a single cylinder-type rotational viscometer. When the viscosity is less than 600 mPa·s, the viscosity may be determined in accordance with "Viscosity measurement by capillary tube viscometer" in "Viscosity Determination" of General Tests described in the Japanese Pharmacopoeia, Sixteenth Edition by using an Ubbelohde-type viscometer.

The alkyl cellulose is pulverized in such a manner as to obtain an average particle size of preferably 1 to 150 μm, more preferably 1 to 50 μm to satisfy the specific surface area of a finally resulting alkyl cellulose. The pulverized alkyl cellulose may be optionally classified through a sieve having a particular mesh size to adjust the particle size and the specific surface area.

The pulverization method and the pulverizer are not particularly limited. To obtain a high specific surface area, preferred are an impact pulverizer such as Turbo Mill (manufactured by TURBO), PPSR (manufactured by PALL-MANN), Victory Mill (manufactured by Hosokawa Micron), Jet-Mill (manufactured by Nippon Pneumatic), Micron Jet Q (manufactured by Hosokawa Micron) and ACM Pulverizer (manufactured by Hosokawa Micron); and a pressure pulverizer such as a vibrating mill, a ball mill, a roller mill and a bead mill. Of these pulverizers, an impact pulverizer such as Jet-Mill, Micron Jet Q and ACM Pulverizer are preferred from the standpoint of a high specific surface area.

The sieve to be used for classification is not particularly limited. The sieve is preferably exemplified by a JIS 200-mesh sieve (a mesh size of 75 μm), a JIS 235-mesh sieve (a mesh size of 63 μm), a JIS 330-mesh sieve (a mesh size of 45 μm) and a JIS 390-mesh sieve (a mesh size of 38 μm).

Since the obtained alkyl cellulose has a high polymerization degree (a viscosity at 20° C. of a 2% by weight aqueous solution of 50 mPa·s or more), it is depolymerized to obtain a low-polymerization-degree alkyl cellulose. The depolymerization method includes depolymerization by hydrolysis with an acid catalyst and depolymerization by oxidative decomposition with an oxidizing agent. The depolymerization method is preferably depolymerization by hydrolysis with an acid catalyst from the standpoint of storage stability.

The acid to be used for the depolymerization by hydrolysis with an acid catalyst is preferably exemplified by an inorganic acid such as hydrochloric acid, sulfuric acid, nitric acid and phosphoric acid. The acid can be used singly or in combination of two or more. The addition of the acid to a system includes addition of the acid in a gas state and in a solution state, and is preferably addition of the acid in a solution state. The amount of the acid to be added is preferably 0.1 to 3.0% by weight, more preferably 0.15 to 1.5% by weight relative to the weight of an alkyl cellulose.

The inside temperature of the reactor during the depolymerization is not particularly limited. It is preferably 50 to 130° C., more preferably 60 to 110° C., even more preferably 60 to 90° C. The depolymerization time is preferably selected according to the viscosity at 20° C. of a 2% by weight aqueous solution of alkyl cellulose before the depolymerization, the viscosity at 20° C. of a 2% by weight aqueous solution of low-polymerization-degree alkyl cellulose after the depolymerization and the depolymerization conditions. The viscosity at 20° C. of a 2% by weight aqueous solution of the low-polymerization-degree alkyl cellulose prepared in this manner is preferably 1 to 15 mPa·s, more preferably 3 to 10 mPa·s.

The low-polymerization-degree alkyl cellulose after the depolymerization may be pulverized to improve the grindability of particles and to facilitate pulverization into fine particles. The pulverized alkyl cellulose may be classified through a sieve having a particular mesh size to adjust the specific surface area. The pulverization method and the pulverizer are not particularly limited. For example, the above mentioned pulverizer may be used. The sieve to be used for the classification is not particularly limited. For example, the above mentioned sieves may be used.

Next, a solid preparation comprising the alkyl cellulose will be described. The alkyl cellulose provides high moldability so that addition of a small amount of the alkyl cellulose can increase the tablet hardness when the tablet is produced by dry direct tableting or dry granulation tableting. In recent years, a tablet is downsized for easy administration so that the amount of a binder or another additive tends to be reduced. Further, in a tablet containing a high content of drug (e.g. a tablet having a drug content of 50% by weight or more), the amount of a binder or another additive is also reduced. For this reason, it is preferred to use a binder that increases the tablet hardness at a small content. The meaning of the low content varies depending on the weight and shape of a tablet, a drug type and the like. The content of the alkyl cellulose in the solid preparation is more than 0% by weight and is preferably 20% by weight or less, more preferably 10% by weight or less, even more preferably 5% by weight or less.

The solid preparation may be produced, for example, by the method comprising the steps of: mixing the obtained alkyl cellulose and a drug or the active ingredient of a health food with a various type of additive commonly used in the fields of pharmaceutical products and foods including health foods, wherein the additive includes an excipient, a disintegrant, a binder, a lubricant, an anti-aggregation agent, and a solubilizing agent for a pharmaceutical compound; and subjecting the resulting mixture to tableting or granulation. The solid preparation includes a tablet, a granule, a powdered drug and a capsule. The alkyl cellulose is also applicable to orally-disintegrating tablets which have been recently intensively studied.

In the present invention, the drug and the active ingredient of a health food to be used for the production of a solid preparation comprising the alkyl cellulose may be any orally administrable drug and any active ingredient of a health food. Examples of the drug include a drug for the central nervous system, a drug for the cardiovascular system, a drug for the respiratory system, a drug for the digestive system, an antibiotic, an antitussive and expectorant, an antihistamine, an antipyretic anti-inflammatory analgesic, a diuretic, an autonomic agent, an antimalarial agent, an antidiarrheal agent, a psychotropic, and vitamins and derivatives thereof. Examples of the health food include foods with nutrient function claims, foods for specified health uses, and foods with functional claims. Examples of the active ingredient in the health food include the above vitamins and derivatives thereof, a mineral, a carotenoid, an amino acid and a derivative thereof, a plant extract, and a health food material.

Examples of the drug for the central nervous system include diazepam, idebenone, aspirin, ibuprofen, paracetamol, naproxen, piroxicam, diclofenac sodium, indomethacin, sulindac, lorazepam, nitrazepam, phenytoin, acetaminophen, ethenzamide, ketoprofen and chlordiazepoxide.

Examples of the drug for the cardiovascular system include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, propranolol hydrochloride and alprenolol hydrochloride.

Examples of the drug for the respiratory system include amlexanox, dextromethorphan, theophylline, pseudoephedrine, salbutamol and guaifenesin.

Examples of the drug for the digestive system include benzimidazole drugs having antiulcer action such as 2-[[3-methyl-4-(2,2,2-trifluoroethoxy)-2-pyridyl]methylsulfinyl] benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cefaclor and erythromycin.

Examples of the antitussive and expectorant include noscapine hydrochloride, carbetapentane citrate, dextromethorphan hydrobromide, isoaminile citrate and dimemorfan phosphate.

Examples of the antihistamine include chlorpheniramine maleate, diphenhydramine hydrochloride and promethazine hydrochloride.

Examples of the antipyretic anti-inflammatory analgesic include ibuprofen, diclofenac sodium, flufenamic acid, sulpyrine, aspirin and ketoprofen.

Examples of the diuretic include caffeine.

Examples of the autonomic agent include dihydrocodeine phosphate, dl-methylephedrine hydrochloride, atropine sulfate, acetylcholine chloride and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate and tranexamic acid.

Examples of the mineral include calcium, magnesium, manganese, zinc, iron, copper, selenium, chromium, sulfur and iodine.

Examples of the carotenoid include β-carotene, α-carotene, lutein, cryptoxanthin, zeaxanthin, lycopene, astaxanthin and Multicarotene.

Examples of the amino acid include aliphatic amino acids, branched-chain amino acids, hydroxyamino acids, acidic amino acids, acidic amino acid amides, basic amino acids, sulfur-containing amino acids, aromatic amino acids, heterocyclic amino acids and imino acids.

Examples of the amino acid derivative include acetylglutamine, acetylcysteine, carboxymethylcysteine, acetyltyrosine, acetylhydroxyproline, 5-hydroxyproline, glutathione, creatine, S-adenosylmethionine, glycylglycine, glycylglutamine, dopa, alanylglutamine, carnitine and γ-aminobutyric acid.

Examples of the plant extract includes aloe extract, propolis extract, *agaricus* extract, *Panax ginseng* extract, ginkgo leaf extract, turmeric extract, curcumin, sprouted brown rice extract, shiitake mycelium extract, *Rubus* suavissimus extract, sweet *Hydrangea* leaf extract, Fomes yucatensis extract, sesame extract, garlic extract, maca (*Lepidium meyenii*) extract, plant worm (*Cordyceps sinensis*) extract, camomile extract and red pepper extract.

Examples of the health food material include royal jelly; dietary fibers; proteins; bifidobacteria; lactic acid bacteria; chitosan; yeast; glucosamine; lecithin; polyphenols; cartilage of animals, fish and shellfish; soft-shelled turtle; lactoferrin; freshwater clams; eicosapentaenoic acid, germanium, enzymes, creatine, carnitine, citric acid, raspberry ketone, coenzyme Q10, methylsulfonylmethane and soybean peptides bonded with phospholipids.

Examples of the excipient include a saccharide such as white soft sugar, lactose and glucose; a sugar alcohol such as mannitol, sorbitol and erythritol; starch; crystalline cellulose; calcium phosphate; and calcium sulfate.

Examples of the disintegrant include low-substituted hydroxypropyl cellulose, carmellose or salts thereof, croscarmellose sodium, sodium carboxymethyl starch, crospovidone, crystalline cellulose, and crystalline cellulose carmellose sodium.

Examples of the binder include polyvinyl alcohol, polyacrylic acid, polymethacrylic acid, polyvinylpyrrolidone, glucose, white soft sugar, lactose, maltose, dextrin, sorbitol, mannitol, macrogols, gum arabic, gelatin, agar, starch, crystalline cellulose, and low-substituted hydroxypropyl cellulose.

Examples of the lubricant and the anti-aggregation agent include talc, magnesium stearate, calcium stearate, colloidal silica, stearic acid, waxes, hardened oil, polyethylene glycols, and sodium benzoate.

Examples of the solubilizing agent for a pharmaceutical compound include organic acids such as fumaric acid, succinic acid, malic acid and adipic acid.

As for the method for producing the solid preparation, for example, a tablet may be produced by any production method of dry direct tableting, dry granulation tableting, wet agitation-granulation tableting, and fluidized bed granulation tableting. Of them, dry direct tableting and dry granulation tableting, in which an alkyl cellulose is used without being dissolved, are particularly preferred.

The dry direct tableting is a method of tableting a mixture prepared by dry blending of an alkyl cellulose, a drug, and for example, an optional excipient, an optional disintegrant and/or an optional lubricant. Since this method contains no granulation step and can be simplified, it is the method of high productivity.

The dry granulation tableting is a method of tableting a granule prepared by compression-granulation of an alkyl cellulose, a drug, and for example, an optional excipient, an optional disintegrant and/or an optional lubricant. This method is effective for a drug susceptible to water or a solvent. The granule may be prepared by roller compression with a compaction granulator such as a roller compactor. The roll pressure varies depending on powder physical properties, and is preferably 1 to 30 MPa, more preferably 2 to 12 MPa. The rotation speed of the roll is preferably 1 to 50 rpm, more preferably 2 to 20 rpm. The rotation speed of the screw is preferably 1 to 100 rpm, more preferably 2 to 50 rpm. Flakes prepared by roller compression may be pulverized and sized with a pulverizer or disintegrator such as Comil, Quick Mill, Power Mill, Granumeister, and Roll Granulator into a powder for tableting.

EXAMPLES

The present invention will next be described in further detail with reference to Examples and Comparative Examples. The invention is not intended to be limited to or by Examples. Many modifications can be made by a person skilled in the art within the technical concept of the present invention.

Example 1

A wood pulp having an intrinsic viscosity of 1,400 ml/g was pulverized with a pulverizer to obtain a cellulose pulp powder. The cellulose pulp powder in an amount corresponding to 6.0 kg of cellulose was placed in an internalstirring pressure-resistant reactor with a jacket. The reactor was vacuumed and purged with nitrogen to remove oxygen thoroughly from the reactor. Next, the inside temperature of the reactor was adjusted to 55° C. with stirring of the inside thereof, and a 49% by weight aqueous sodium hydroxide solution was added thereto as a first alkali metal hydroxide solution at an addition rate of 12.04 [mol/mol·hr] in such an amount that a molar ratio of the first sodium hydroxide to the cellulose (first sodium hydroxide/cellulose) became 3.01, to obtain alkali cellulose.

Then 2.4 kg of dimethyl ether was added to the reactor, and the inside temperature of the reactor was controlled to maintain the inside temperature at 60° C. After the addition of dimethyl ether, the inside temperature of the reactor was increased from 60° C. to 80° C., while adding methyl chloride to the reactor over 60 minutes in such an amount that a molar ratio of methyl chloride to the total amount of the first and second sodium hydroxides (methyl chloride/total sodium hydroxide) became 1.1, to obtain a first reaction mixture. Subsequently to the addition of methyl chloride, a 49% by weight sodium hydroxide solution was added to the reactor as a second alkali metal hydroxide solution at an addition rate of 2.58 [mol/mol·hr] in such an amount that a molar ratio of the second sodium hydroxide to the cellulose (second sodium hydroxide/cellulose) became 1.26, to obtain a second reaction mixture. The inside temperature of the reactor was 81° C. at the start of the addition of the second sodium hydroxide solution, and 89° C. at the completion of the addition, while increasing the inside temperature of the reactor at an increase rate of 16.4° C./hr from the start to the completion of the addition of the second aqueous sodium hydroxide solution. After the completion of the addition of the second aqueous sodium hydroxide solution, the stirring was continued for 30 minutes to complete the etherification. The ratio of the weight of the first sodium hydroxide in the first aqueous sodium hydroxide solution to the total weight of the first and second sodium hydroxides in the first and second aqueous sodium hydroxide solutions was 70.5%.

The obtained second reaction mixture was subjected to addition of hot water of 95° C. to become a slurry, then washed by using a rotary pressure filter, dried with an air dryer, and pulverized with a ball mill to obtain methyl cellulose. The methyl cellulose had a degree of substitution (DS) of methoxy group of 1.85.

The obtained methyl cellulose was subjected to addition of a 10% by weight aqueous hydrochloric acid solution in such an amount that the HCl component became 0.3% by weight relative to the amount of the methyl cellulose. The depolymerization was carried out for 90 minutes while adjusting the inside temperature of the reactor to 82° C., to obtain low-polymerization-degree methyl cellulose.

The low-polymerization-degree methyl cellulose was pulverized with a high speed rotary impact mill Victory Mill, having a screen with a mesh size of 0.3 mm, to obtain intended pulverized low-polymerization-degree methyl cellulose. The specific surface area, the dissolution start temperature of a 12% by weight aqueous dispersion, the viscosity at 20° C. of a 2% by weight aqueous solution, the average particle size, and the loose bulk density of the obtained low-polymerization-degree methyl cellulose were determined by the following measurements, and are shown in Table 1.

<Measurements of Physical Properties>
(a) Specific Surface Area by BET Method (Multipoint BET Method)

The specific surface area by BET method (multipoint BET method) was determined in accordance with "Method 2: The volumetric method" in "Specific Surface Area by Gas Adsorption" of General Tests described in the Japanese Pharmacopoeia Sixteenth Edition, using an automatic specific surface area/pore distribution analyzer TriStar II 3020 (manufactured by Micromeritics) and the gas adsorption method (adsorption gas: nitrogen; refrigerant: liquid nitrogen) within a relative pressure ($P/P_0$) of 0.05 to 0.30, wherein $P_0$ represents a saturated vapor pressure and P represents a measured equilibrium pressure. A sample had been allowed to stand at 105° C. for 2 hours to be absolutely dried before the measurement. The sample amount varied with measurement samples, and each sample of about 0.5 to 2.0 g was subjected to the measurement.

(b) Viscosity at 20° C. of 2% by Weight Aqueous Solution

When the viscosity at 20° C. of a 2% by weight aqueous solution was 600 mPa·s or more, the viscosity was determined in accordance with "Viscosity measurement by rotational viscometer" in "Viscosity Determination" of General Tests described in the Japanese Pharmacopoeia Sixteenth Edition, using a single cylinder-type rotational viscometer. When the viscosity at 20° C. of a 2% by weight aqueous solution was less than 600 mPa·s, the viscosity was determined in accordance with "Viscosity measurement by capillary tube viscometer" in "Viscosity Determination" of General Tests described in the Japanese Pharmacopoeia Sixteenth Edition, using an Ubbelohde-type viscometer.

(c) Dissolution Start Temperature

The dissolution start temperature was determined by the above mentioned method for methyl cellulose having such a concentration that 12% by weight aqueous methyl cellulose solution was obtained as a result of complete dissolution of the methyl cellulose.

(d) Average Particle Size

The volume average particle size was determined with a MASTERSIZER 3000 (manufactured by Malvern) by laser diffractometry (analysis: Fraunhofer approximation) in conditions of a dispersion pressure of 2 to 3 bar and a scattering intensity of 2 to 10%.

(e) Loose Bulk Density

The loose bulk density was determined with a Powder Tester PT-S (manufactured by Hosokawa Micron) by the following procedure. A sample sieved through a JIS 22-mesh sieve (a mesh size of 710 μm) was evenly placed in a cylindrical container being made of stainless steel and having a diameter of 5.03 cm and a height of 5.03 cm (a capacity of 100 ml) from 23 cm above the top surface of the container; and then the top surface was leveled off for weighing.

(f) Hardness and Disintegration Time of Tablet

The obtained methyl cellulose and the other components in the following tablet formulation except the magnesium stearate were mixed in a polyethylene bag for 3 minutes, then subjected to addition of the magnesium stearate, and mixed for 30 seconds. The resulting mixture was subjected to dry direct tableting in the following tableting conditions to produce tablets. A load was applied to the produced tablet at a speed of 1 mm/sec in a diameter direction of the tablet with a tablet hardness tester (TM5-1 manufactured by Kikusui Seisakusho), and the maximum breaking strength at the time when the tablet was broken was recorded as the tablet hardness. The disintegration time (test liquid: water) was evaluated in accordance with the Japanese Pharmacopoeia Sixteenth Edition. The results are shown in Table 1.

Tablet Formulation

| | |
|---|---|
| Acetaminophen coarse particles (type S, manufactured by Yamamoto Chemical) | 50.0 parts by weight |
| Lactose hydrate (Dilactose S, manufactured by Freund Corporation) | 40.0 parts by weight |
| Low-substituted hydroxypropyl cellulose (NBD-021, manufactured by Shin-Etsu Chemical) | 5.0 parts by weight |
| Methyl cellulose | 5.0 parts by weight |
| Magnesium stearate | 0.5 part by weight |

Tableting Conditions

Tableting machine: Rotary tableting machine (VIRGO, manufactured by Kikusui Seisakusho)
Tablet size: 200 mg/tablet, 8 mm-D, 12 mm-R
Tableting pressure: 10 kN
Tableting speed: 20 rpm Example 2

Intended pulverized low-polymerization-degree methyl cellulose was obtained in the same manner as in Example 1 except that the low-polymerization-degree methyl cellulose obtained in Example 1 was pulverized with an air flow impact mill Jet Mill (Labo Jet Mill, manufactured by Nippon Pneumatic) in the conditions of a milling pressure of 0.35 MPa, a classification zone clearance of 20 mm and a louver size of large. Powder physical properties of the pulverized low-polymerization-degree methyl cellulose, and tablet physical properties of tablets produced therefrom by dry direct tableting in the same manner as in Example 1 are shown in Table 1.

Example 3

Intended pulverized low-polymerization-degree methyl cellulose was obtained in the same manner as in Example 2 except that as the pulverization conditions with an air flow impact mill Jet Mill, a milling pressure of 0.45 MPa, a classification zone clearance of 35 mm and a louver size of large were used. Powder physical properties of the pulverized low-polymerization-degree methyl cellulose, and tablet physical properties of tablets produced therefrom by dry direct tableting in the same manner as in Example 1 are shown in Table 1.

Example 4

Intended pulverized low-polymerization-degree methyl cellulose was obtained in the same manner as in Example 1 except that the low-polymerization-degree methyl cellulose obtained in Example 1 was pulverized with an ACM Pulverizer (ACM-15H, manufactured by Hosokawa Micron) in the conditions of a pulverization section rotation speed of 7,800 rpm, a classifier rotation speed of 7,000 rpm, and a blower rate of 10 m³/min. Powder physical properties of the pulverized low-polymerization-degree methyl cellulose, and tablet physical properties of tablets produced therefrom by dry direct tableting in the same manner as in Example 1 are shown in Table 1.

Example 5

Intended pulverized low-polymerization-degree methyl cellulose was obtained in the same manner as in Example 2 except that as the pulverization conditions with an air flow impact mill Jet Mill, a milling pressure of 0.5 MPa, a classification zone clearance of 35 mm and a louver size of small were used. Powder physical properties of the pulverized low-polymerization-degree methyl cellulose, and tablet physical properties of tablets produced therefrom by dry direct tableting in the same manner as in Example 1 are shown in Table 1.

Example 6

Low-polymerization-degree methyl cellulose was obtained in the same manner as in Example 1 except that the period of time for depolymerizing the methyl cellulose obtained in Example 1 was changed to 60 minutes. The obtained low-polymerization-degree methyl cellulose was pulverized with an air flow impact mill Jet Mill (Labo Jet Mill, manufactured by Nippon Pneumatic) in the conditions of a milling pressure of 0.4 MPa, a classification zone clearance of 15 mm and a louver size of large. Powder physical properties of the pulverized low-polymerization-degree methyl cellulose, and tablet physical properties of tablets produced therefrom by dry direct tableting in the same manner as in Example 1 are shown in Table 1.

Example 7

A cellulose pulp was placed in a reactor in the same manner as in Example 1. The inside temperature of the reactor was adjusted to 60° C. with stirring of the inside thereof, and a 49% by weight aqueous sodium hydroxide solution was added thereto as a first alkali metal hydroxide solution at an addition rate of 10.48 [mol/mol·hr] in such an amount that a molar ratio of the first sodium hydroxide to the cellulose (first sodium hydroxide/cellulose) became 2.62, to obtain alkali cellulose.

Subsequently, a first reaction mixture was obtained in the same manner as in Example 1. Next, a second reaction mixture was obtained in the same manner as in Example 1 except that the inside temperature of the reactor was 77° C. at the start of the addition of the second aqueous sodium hydroxide solution, and 89° C. at the completion of the addition, while increasing the inside temperature of the reactor at an increase rate of 24° C./hr from the start to the completion of the addition of the second aqueous sodium hydroxide solution. The second aqueous sodium hydroxide solution was added at an addition rate of 3.20 [mol/mol·hr] in such an amount that a molar ratio of the second sodium hydroxide to the cellulose (second sodium hydroxide/cellulose) became 1.60. The ratio of the weight of the first sodium hydroxide in the first aqueous sodium hydroxide solution to the total weight of the first and second sodium hydroxides in the first and second aqueous sodium hydroxide solutions was 62.1%.

The obtained second reaction mixture was then purified and pulverized in the same manner as in Example 1 to obtain methyl cellulose. The methyl cellulose had a degree of substitution (DS) of methoxy group of 1.81.

The obtained methyl cellulose was subjected to addition of a 10% by weight aqueous hydrochloric acid solution in such an amount that the HCl component became 0.3% by weight relative to the methyl cellulose. The depolymerization was carried out for 90 minutes while adjusting the inside temperature of the reactor to 82° C., to obtain low-polymerization-degree methyl cellulose.

The low-polymerization-degree methyl cellulose was pulverized with an air flow impact mil Jet Mill (Labo Jet Mill, manufactured by Nippon Pneumatic) in the same manner as in Example 2, to obtain intended pulverized low-polymerization-degree methyl cellulose. Powder physical properties of the pulverized low-polymerization-degree methyl cellulose, and tablet physical properties of tablets produced therefrom by dry direct tableting in the same manner as in Example 1 are shown in Table 1.

Example 8

A cellulose pulp was placed in a reactor in the same manner as in Example 1. The inside temperature of the reactor was adjusted to 55° C. with stirring of the inside thereof, and a 49% by weight aqueous sodium hydroxide solution was added thereto as a first alkali metal hydroxide solution at an addition rate of 9.04 [mol/mol·hr] in such an amount that a molar ratio of the first sodium hydroxide to the cellulose (first sodium hydroxide/cellulose) became 2.26, to obtain alkali cellulose.

Subsequently, a first reaction mixture was obtained in the same manner as in Example 1. Next, a second reaction mixture was obtained in the same manner as in Example 1 except that the inside temperature of the reactor was 80° C. at the start of the addition of the second aqueous sodium hydroxide solution, and 92° C. at the completion of the addition, while increasing the inside temperature of the reactor at an increase rate 36° C./hr from the start to the completion of the addition of the second aqueous sodium hydroxide solution. The second aqueous sodium hydroxide solution was added at an addition rate of 5.52 [mol/mol·hr] in such an amount that a molar ratio of the second sodium hydroxide to the cellulose (second sodium hydroxide/cellulose) became 1.84. The ratio of the weight of the first sodium hydroxide in the first aqueous sodium hydroxide solution to the total weight of the first and second sodium hydroxides in the first and second aqueous sodium hydroxide solutions was 55.1%.

The obtained second reaction mixture was then purified and pulverized in the same manner as in Example 1 to obtain methyl cellulose. The methyl cellulose had a degree of substitution (DS) of methoxy group of 1.85.

The obtained methyl cellulose was subjected to addition of a 10% by weight aqueous hydrochloric acid solution in such an amount that the HCl component became 0.3% by weight relative to the methyl cellulose. The depolymerization was carried out for 90 minutes while adjusting the inside temperature of the reactor to 82° C., to obtain low-polymerization-degree methyl cellulose.

The low-polymerization-degree methyl cellulose was pulverized with an air flow impact mill Jet Mill (Labo Jet Mill, manufactured by Nippon Pneumatic) in the same manner as in Example 2, to obtain intended pulverized low-polymerization-degree methyl cellulose. Powder physical properties of the pulverized low-polymerization-degree methyl cellulose, and tablet physical properties of tablets produced therefrom by dry direct tableting in the same manner as in Example 1 are shown in Table 1.

Comparative Example 1

A cellulose pulp was placed in a reactor in the same manner as in Example 1. The inside temperature of the reactor was adjusted to 60° C. with stirring of the inside thereof, and a 49% by weight aqueous sodium hydroxide solution was added thereto at an addition rate of 18.88 [mol/mol·hr], without dividing the aqueous sodium hydroxide solution, in such an amount that a molar ratio of the sodium hydroxide to the cellulose (sodium hydroxide/cellulose) became 4.72, to obtain alkali cellulose.

Then 2.4 kg of dimethyl ether was added to the reactor, and the inside temperature of the reactor was controlled to maintain the inside temperature at 60° C. After the addition of dimethyl ether, the inside temperature of the reactor was increased from 60 to 80° C., while adding methyl chloride to the reactor over 60 minutes in such an amount that a molar ratio of the methyl chloride to the sodium hydroxide (methyl chloride/sodium hydroxide) became 1.1. Subsequent to the addition of methyl chloride, etherification was carried out for 70 minutes, while increasing the inside temperature of the reactor from 80° C. to 95° C., to obtain crude methyl cellulose.

The crude methyl cellulose was then purified and pulverized in the same manner as in Example 1 to obtain methyl cellulose. The methyl cellulose had a degree of substitution (DS) of methoxy group of 1.81.

The obtained methyl cellulose was subjected to addition of a 10% by weight aqueous hydrochloric acid solution in such an amount that the HCl component became 0.3% by weight relative to the methyl cellulose. The depolymerization was carried out for 70 minutes, while adjusting the inside temperature of the reactor to 80° C., to obtain low-polymerization-degree methyl cellulose. Powder physical properties of the low-polymerization-degree methyl cellulose, and tablet physical properties of tablets produced therefrom by dry direct tableting in the same manner as in Example 1 are shown in Table 1.

Comparative Example 2

Low-polymerization-degree methyl cellulose was obtained in the same manner as in Example 1, but not pulverized with a high speed rotary impact mill Victory Mill. In other words, the low-polymerization-degree methyl cellulose was obtained as methyl cellulose having a low specific surface area. Powder physical properties of the low-polymerization-degree methyl cellulose, and tablet physical properties of tablets produced therefrom by dry direct tableting in the same manner as in Example 1 are shown in Table 1.

Comparative Example 3

The low-polymerization-degree methyl cellulose obtained in Comparative Example 1 was pulverized with a high speed rotary impact mill Victory Mill, having a screen with a mesh size of 0.3 mm, to obtain pulverized low-polymerization-degree methyl cellulose. Powder physical properties of the pulverized low-polymerization-degree methyl cellulose, and tablet physical properties of tablets produced therefrom by dry direct tableting in the same manner as in Example 1 are shown in Table 1.

Comparative Example 4

The low-polymerization-degree methyl cellulose obtained in Comparative Example 1 was pulverized in the same manner as in Comparative Example 3 except that an air flow impact mill Jet Mill (Labo Jet Mill, manufactured by Nippon Pneumatic) was used in conditions of a milling pressure of 0.35 MPa, a classification zone clearance of 20 mm and a louver size of large, to obtain pulverized low-polymerization-degree methyl cellulose. Powder physical properties of the pulverized low-polymerization-degree methyl cellulose, and tablet physical properties of tablets produced therefrom by dry direct tabletting in the same manner as in Example 1 are shown in Table 1.

Comparative Example 5

The pulverized low-polymerization-degree methyl cellulose was obtained in the same manner as in Comparative Example 4 except that as the pulverization conditions for an air flow impact mill Jet Mill, a milling pressure of 0.45 MPa, a classification zone clearance of 35 mm and louver size of large were used. Powder physical properties of the pulverized low-polymerization-degree methyl cellulose, and tablet physical properties of tablets produced therefrom by dry direct tabletting in the same manner as in Example 1 are shown in Table 1.

Powder Mixture Formulation

| | |
|---|---|
| Acetaminophen fine powder (manufactured by Yamamoto Chemical) | 50.0 parts by weight |
| Lactose hydrate (Pharmatose 200M, manufactured by DMV Pharma) | 39.0 parts by weight |
| Methyl cellulose | 10.0 parts by weight |
| Light anhydrous silicic acid | 0.5 part by weight |
| Magnesium stearate | 0.5 part by weight |

The 95 parts by weight of the obtained granule and 5 parts by weight of low-substituted hydroxypropyl cellulose (NBD-021, manufactured by Shin-Etsu Chemical Co., Ltd.) were mixed in a polyethylene bag for 3 minutes, then subjected to addition of 0.5 part by weight of magnesium stearate and mixed for 30 seconds. The resulting mixture

TABLE 1

| | production | | powder properties | | | | | tablet properties | |
|---|---|---|---|---|---|---|---|---|---|
| | Addition of NaOH | weight ratio of first NaOH *1 (%) | specific surface area (m²/g) | dissolution start temp. (° C.) | viscosity of aq. 2 wt % solution (mPa·s) | average Particle Size (μm) | loose bulk density (g/mL) | tablet hardness (N) | disintegration time (min) |
| Example 1 | 2 stages | 70.5 | 0.90 | 22.6 | 4.18 | 48.8 | 0.21 | 37.0 | 0.9 |
| Example 2 | 2 stages | 70.5 | 2.52 | 21.5 | 4.11 | 19.2 | 0.11 | 41.7 | 1.3 |
| Example 3 | 2 stages | 70.5 | 3.81 | 23.1 | 4.09 | 11.3 | 0.07 | 51.7 | 1.4 |
| Example 4 | 2 stages | 70.5 | 1.97 | 20.3 | 3.95 | 20.1 | 0.20 | 41.0 | 1.4 |
| Example 5 | 2 stages | 70.5 | 2.73 | 22.5 | 6.27 | 19.9 | 0.09 | 45.0 | 1.2 |
| Example 6 | 2 stages | 70.5 | 6.52 | 25.6 | 3.77 | 4.3 | 0.06 | 74.0 | 1.7 |
| Example 7 | 2 stages | 62.1 | 2.44 | 16.4 | 4.21 | 20.5 | 0.13 | 40.9 | 1.1 |
| Example 8 | 2 stages | 55.1 | 2.63 | 6.2 | 3.89 | 18.9 | 0.10 | 42.5 | 0.9 |
| Comp. Ex. 1 | 1 stage | 100.0 | 0.44 | 29.5 | 4.13 | 82.1 | 0.33 | 27.1 | 1.2 |
| Comp. Ex. 2 | 2 stages | 70.5 | 0.42 | 22.4 | 4.21 | 86.4 | 0.32 | 28.6 | 0.9 |
| Comp. Ex. 3 | 1 stage | 100.0 | 0.75 | 30.1 | 4.10 | 52.1 | 0.29 | 29.2 | 1.2 |
| Comp. Ex. 4 | 1 stage | 100.0 | 1.91 | 28.8 | 4.14 | 18.3 | 0.19 | 37.0 | 2.3 |
| Comp. Ex. 5 | 1 stage | 100.0 | 3.57 | 30.7 | 4.09 | 9.4 | 0.11 | 49.8 | 3.1 |

*1 The ratio of weight of first NaOH to total weight of first and second NaOH is shown.

It is evident from Table 1 that the tablets produced by dry direct tabletting in Examples 1 to 8, using the tablet formulation containing the pulverized low-polymerization-degree methyl cellulose of Examples 1 to 8, show higher tablet hardness values than those in Comparative Examples 1 to 3. The pulverized low-polymerization-degree methyl cellulose in Example 1 shows a lower dissolution start temperature than that of the methyl cellulose of Comparative Example 3, so that the tablet of Example 1 shows a shorter disintegration time in spite of higher tablet hardness than the tablet hardness of Comparative Example 3. Similarly, the tablets in Examples 2 to 8 show shorter disintegration times than those in Comparative Examples 4 to 5.

Example 9

The methyl cellulose obtained in Example 2 and the other components in the following powder mixture formulation except the magnesium stearate were mixed in a polyethylene bag for 3 minutes, then subjected to addition of the magnesium stearate, and mixed for 30 seconds. The resulting mixture was compression molded with a roller compactor (TF-MINI, manufactured by Freund Corporation) at a roll pressure of 6 MPa, a roll rotation speed of 10 rpm and a screw rotation speed of 10 rpm, and then subjected to regulating of granule sizes with a roll granulator (GRN-T54S, manufactured by Nippon Granulator) to obtain dry granules.

was subjected to tabletting in the following tabletting conditions to produce tablets. The tablet hardness and the disintegration time of the produced tablets were evaluated by the above-mentioned methods, and the results are shown in Table 2.

Tabletting Conditions
Tabletting machine: Rotary tabletting machine (VIRGO, manufactured by Kikusui Seisakusho)
Tablet size: 200 mg/tablet, 8 mm-D, 12 mm-R
Tabletting pressure: 7.5 kN
Tabletting speed: 20 rpm Example 10

The dry granulation and tabletting were carried out in the same manner as in Example 9 except that the pulverized low-polymerization-degree methyl cellulose obtained in Example 3 was used as the methyl cellulose, to produce tablets. The tablet hardness and the disintegration time of the produced tablets were evaluated, and the results are shown in Table 2.

Comparative Example 6

The dry granulation and tabletting were carried out in the same manner as in Example 9 except that the low-polymerization-degree methyl cellulose obtained in Comparative Example 2 was used as the methyl cellulose, to produce tablets. The tablet hardness and the disintegration time of the produced tablets were evaluated, and the results are shown in Table 2.

Comparative Example 7

The dry granulation and tableting were carried out in the same manner as in Example 9 except that the pulverized low-polymerization-degree methyl cellulose obtained in Comparative Example 4 was used as the methyl cellulose, to produce tablets. The tablet hardness and the disintegration time (test liquid: water) of the produced tablets were evaluated, and the results are shown in Table 2.

Comparative Example 8

The dry granulation and tableting were carried out in the same manner as in Example 9 except that the pulverized low-polymerization-degree methyl cellulose obtained in Comparative Example 5 was used as the methyl cellulose, to produce tablets. The tablet hardness and the disintegration time (test liquid: water) of the produced tablets were evaluated, and the results are shown in Table 2.

TABLE 2

| | | tablet properties | |
|---|---|---|---|
| | type of methyl cellulose (MC) | tablet hardness (N) | disintegration time (min) |
| Example 9 | pulverized low-polymerization-degree MC in Example 2 | 38.4 | 1.1 |
| Example 10 | pulverized low-polymerization-degree MC in Example 3 | 56.1 | 5.0 |
| Comp. Ex. 6 | low-polymerization-degree MC in Comp. Ex. 2 | 25.2 | 0.4 |
| Comp. Ex. 7 | pulverized low-polymerization-degree MC in Comp. Ex. 4 | 35.4 | 11.2 |
| Comp. Ex. 8 | pulverized low-polymerization-degree MC in Comp. Ex. 5 | 49.6 | 28.1 |

It is evident from Table 2 that the tablets produced by dry granulation tableting in Examples 9 and 10, using the table formulations containing the pulverized low-polymerization-degree methyl celluloses of Examples 2 and Example 3, respectively, show higher tablet hardness values than that in Comparative Example 6. The tablets in Examples 9 and 10 are disintegrated rapidly in spite of high tablet hardness values approximately equal to those in Comparative Examples 7 and 8.

The invention claimed is:

1. A solid preparation comprising:
   an alkyl cellulose having a specific surface area determined by BET method of 0.5 to 10.0 $m^2/g$ and a dissolution start temperature of 5 to 27° C.

2. The solid preparation according to claim 1, wherein a 2% by weight aqueous solution of the alkyl cellulose has a viscosity of 1 to 15 mPa·s at 20° C.

3. The solid preparation according to claim 1, wherein the alkyl cellulose has a volume average particle size determined by dry laser diffractometry of 1 to 50 μm.

4. The solid preparation according to claim 2, wherein the alkyl cellulose has a volume average particle size determined by dry laser diffractometry of 1 to 50 μm.

5. The solid preparation according to claim 1, wherein the alkyl cellulose has a loose bulk density of 0.01 to 0.30 g/mL.

6. The solid preparation according to claim 1, wherein the alkyl cellulose has a degree of substitution (DS) of alkyl group of 1.61 to 2.03.

7. The solid preparation according to claim 1, wherein the alkyl cellulose is methyl cellulose.

8. The solid preparation according to claim 1, wherein the alkyl cellulose comprised by the solid preparation is in an amount of more than 0% by weight but not more than 20% by weight.

9. A method for producing a solid preparation, comprising the steps of:
   mixing a cellulose pulp and a first alkali metal hydroxide solution with stirring to obtain alkali cellulose;
   reacting the alkali cellulose with an alkylating agent to obtain a first reaction mixture;
   mixing the first reaction mixture and a second alkali metal hydroxide solution with stirring and without further addition of any alkylating agent to obtain a second reaction mixture;
   isolating an alkyl cellulose from the second reaction mixture, wherein the isolated alkyl cellulose has a specific surface area determined by BET method of 0.5 to 10.0 $m^2/g$ and a dissolution start temperature of 5 to 27° C.;
   pulverizing the alkyl cellulose to obtain a pulverized alkyl cellulose;
   depolymerizing the pulverized alkyl cellulose to obtain a low-polymerization-degree alkyl cellulose;
   pulverizing the low-polymerization-degree alkyl cellulose to obtain a pulverized low-polymerization-degree alkyl cellulose; and
   subjecting a mixture or granule containing the pulverized low-polymerization-degree alkyl cellulose and a drug to dry direct tableting or dry granulation tableting;
   wherein a ratio of a weight of a first alkali metal hydroxide in the first alkali metal hydroxide solution to a total weight of the first alkali metal hydroxide in the first alkali metal hydroxide solution and a second alkali metal hydroxide in the second alkali metal hydroxide solution is 50 to 86%.

* * * * *